(12) United States Patent
Toriumi

(10) Patent No.: US 9,126,900 B2
(45) Date of Patent: Sep. 8, 2015

(54) PROCESS FOR PRODUCING MANDELONITRILE COMPOUND

(75) Inventor: Tatsuya Toriumi, Oita (JP)

(73) Assignee: Sumitomo Chemical Company, Limited, Tokyo (JP)

(*) Notice: Subject to any disclaimer, the term of this patent is extended or adjusted under 35 U.S.C. 154(b) by 0 days.

(21) Appl. No.: 14/110,940

(22) PCT Filed: Mar. 26, 2012

(86) PCT No.: PCT/JP2012/058772
§ 371 (c)(1),
(2), (4) Date: Oct. 11, 2013

(87) PCT Pub. No.: WO2012/141015
PCT Pub. Date: Oct. 18, 2012

(65) Prior Publication Data
US 2014/0031576 A1    Jan. 30, 2014

(30) Foreign Application Priority Data
Apr. 12, 2011   (JP) .................................. 2011-088128

(51) Int. Cl.
C07C 253/10    (2006.01)
C07C 253/30    (2006.01)
C07C 253/08    (2006.01)

(52) U.S. Cl.
CPC .............. *C07C 253/30* (2013.01); *C07C 253/08* (2013.01)

(58) Field of Classification Search
CPC .................................................... C07C 253/30
USPC .................................................. 558/351, 315
See application file for complete search history.

(56) References Cited

U.S. PATENT DOCUMENTS

| 4,175,093 A | 11/1979 | Reinink et al. |
| 5,145,980 A | 9/1992 | Wenderoth et al. |
| 6,653,498 B2 * | 11/2003 | Kirschbaum et al. ......... 558/351 |
| 8,129,560 B2 | 3/2012 | Bowden et al. |
| 8,309,752 B2 | 11/2012 | Ishida et al. |
| 8,309,753 B2 * | 11/2012 | Nakazawa ..................... 558/351 |
| 2011/0034718 A1 | 2/2011 | Nakazawa |

FOREIGN PATENT DOCUMENTS

| CN | 1062348 A | 7/1992 |
| CN | 1789238 A | 6/2006 |
| JP | S54-59249 A | 5/1979 |
| JP | H06-271522 A | 9/1994 |
| JP | H07-70040 A | 3/1995 |
| JP | H09-95462 A | 4/1997 |
| JP | 2007-277534 A | 10/2007 |
| JP | 2009-256262 A | 11/2009 |
| JP | 2010-030982 A | 2/2010 |

OTHER PUBLICATIONS

Int'l Search Report issued May 29, 2012 in Int'l Application No. PCT/JP2012/058772.
Int'l Preliminary Report on Patentability issued Oct. 24, 2013 in Int'l Application No. PCT/JP2012/058772.
Office Action issued Jan. 6, 2015 in JP Application No. 2011-088128.

* cited by examiner

*Primary Examiner* — Nyeemah A Grazier
(74) *Attorney, Agent, or Firm* — Panitch Schwarze Belisario & Nadel LLP

(57) ABSTRACT

A process for producing a mandelonitrile compound represented by the following formula (2), comprising a step of reacting a benzaldehyde compound represented by the following formula (1) with at least one member selected from the group consisting of metal cyanides and hydrogen cyanide in the presence of a phase transfer catalyst in a solvent.

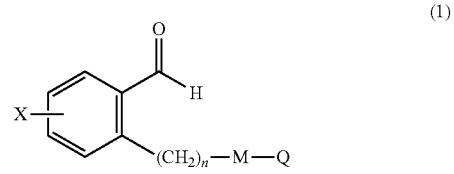

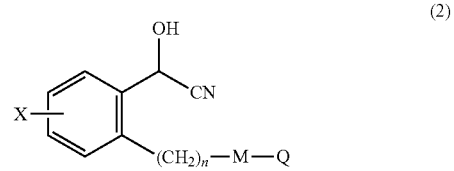

11 Claims, No Drawings

PROCESS FOR PRODUCING MANDELONITRILE COMPOUND

CROSS-REFERENCE TO RELATED APPLICATION

This application is a Section 371 of International Application No. PCT/JP2012/058772, filed Mar. 26, 2012, which was published in the Japanese language on Oct. 18, 2012, under International Publication No. WO 2012/141015 A1, and the disclosure of which is incorporated herein by reference.

TECHNICAL FIELD

The present invention relates to a process for producing a mandelonitrile compound.

BACKGROUND ART

A mandelonitrile compound represented by formula (2):

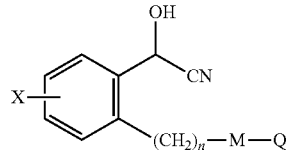

(2)

wherein Q represents an optionally substituted hydrocarbon group having 1 to 14 carbon atoms, an optionally substituted heterocyclic group having 3 to 12 carbon atoms, an optionally substituted methyleneamino group, an optionally substituted acyl group having 2 to 15 carbon atoms or an optionally substituted substituted-sulfonyl group having 1 to 14 carbon atoms, X represents a hydrogen atom, a halogen atom, an optionally substituted alkyl group having 1 to 8 carbon atoms or an optionally protected hydroxyl group, M represents an oxy group (—O—), a thio group (—S—), a sulfinyl group (—SO—), a sulfonyl group (—$SO_2$—), —$NR^1$— or a single bond, $R^1$ represents a hydrogen atom, an alkyl group having 1 to 8 carbon atoms or an acyl group having 1 to 9 carbon atoms, and n represents 0, 1 or 2,
such as 2-(2,5-dimethylphenoxymethyl)mandelonitrile is, for example, useful as a production raw material or a production intermediate of medical and agricultural chemicals.

As a process for producing a mandelonitrile compound, for example, Patent document 1 describes a method of obtaining 2-(2,4-dimethylphenoxymethyl)benzaldehyde cyanohydrin by mixing 2-(2,4-dimethylphenoxymethyl)benzaldehyde, potassium cyanide and ammonium chloride in a mixed solvent composed of an ether and water. Patent document 2 describes a method of obtaining 2-(4-chloro-α-methylbenzylideneaminooxymethyl)benzaldehyde cyanohydrin by mixing 2-(4-chloro-α-methylbenzylideneaminooxymethyl)benzaldehyde, sodium cyanide and sodium bisulfite in a mixed solvent composed of methanol and water.

PRIOR ART DOCUMENTS

Patent Document

[Patent document 1] U.S. Pat. No. 5,145,980 (METHOD 8)
[Patent document 2] JP-A No. 9-95462 (Example 11)

SUMMARY OF THE INVENTION

Problem to be Solved by the Invention

The methods described in Patent documents 1 and 2 were not necessarily fully satisfactory production processes because of the low yield of a mandelonitrile compound.

Means for Solving the Problem

The present inventors have intensively investigated, leading to the present invention.
That is, the present invention is as described below.
[1] A process for producing a mandelonitrile compound represented by formula (2):

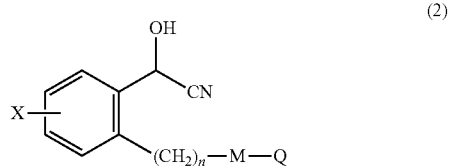

(2)

wherein Q represents an optionally substituted hydrocarbon group having 1 to 14 carbon atoms, an optionally substituted heterocyclic group having 3 to 12 carbon atoms, an optionally substituted methyleneamino group, an optionally substituted acyl group having 2 to 15 carbon atoms or an optionally substituted substituted-sulfonyl group having 1 to 14 carbon atoms, X represents a hydrogen atom, a halogen atom, an optionally substituted alkyl group having 1 to 8 carbon atoms or an optionally protected hydroxyl group, M represents an oxy group (—O—), a thio group (—S—), a sulfinyl group (—SO—), a sulfonyl group (—$SO_2$—), —$NR^1$— or a single bond, $R^1$ represents a hydrogen atom, an alkyl group having 1 to 8 carbon atoms or an acyl group having 1 to 9 carbon atoms, and n represents 0, 1 or 2,
comprising a step of reacting a benzaldehyde compound represented by formula (1):

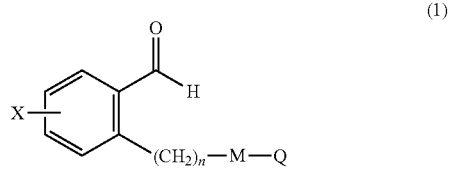

(1)

wherein Q, X, M and n are each as described above, with at least one member selected from the group consisting of metal cyanides and hydrogen cyanide in the presence of a phase transfer catalyst in a solvent.
[2] The process according to [1], wherein the solvent contains an alcohol.
[3] The process according to [1], wherein the solvent is a mixed solvent composed of water, an alcohol, and at least one member selected from the group consisting of aromatic hydrocarbons, aliphatic hydrocarbons and halogenated hydrocarbons.
[4] The process according to [3], wherein the pH of the solvent is one adjusted to 6 to 8.
[5] The process according to [4], wherein the pH of the solvent is one adjusted to 6 to 8 by mixing with acetic acid or hydrochloric acid.

The process according to any one of [1] to [5], wherein the phase transfer catalyst is a quaternary ammonium salt, a quaternary phosphonium salt or a crown ether.

[7] The process according to any one of [1] to [5], wherein the phase transfer catalyst is at least one member selected from the group consisting of tetra-n-butylammonium bromide, benzyltriethylammonium chloride and methyltributylammonium chloride.

[8] The process according to any one of [1] to [7], wherein the use amount of the at least one member selected from the group consisting of metal cyanides and hydrogen cyanide is in the range of 1.2 mole to 3.0 mole with respect to 1 mole of the benzaldehyde compound represented by formula (1).

[9] The process according to any one of [1] to [8], wherein Q is an optionally substituted phenyl group, X is a hydrogen atom, M is an oxy group (—O—) and n is 1 in formulae (1) and (2).

[10] A process for producing the mandelonitrile compound represented by formula (2), comprising a mixing step of mixing the benzaldehyde compound represented by formula (1), at least one member selected from the group consisting of metal cyanides and hydrogen cyanide, a phase transfer catalyst, at least one member selected from the group consisting of aromatic hydrocarbons, aliphatic hydrocarbons and halogenated hydrocarbons, water and an alcohol, and a step of adding an acid to the mixed liquid obtained in the above-described mixing step, thereby maintaining the pH of the aqueous layer of the mixed liquid at 6 to 8.

[11] The process according to [10], wherein the acid is acetic acid or hydrochloric acid.

[12] The process according to [10], wherein the phase transfer catalyst is a quaternary ammonium salt, a quaternary phosphonium salt or a crown ether.

[13] The process according to [11], wherein the phase transfer catalyst is at least one member selected from the group consisting of tetra-n-butylammonium bromide, benzyltriethylammonium chloride and methyltributylammonium chloride.

[14] The process according to any one of [10] to [13], wherein the use amount of the at least one member selected from the group consisting of metal cyanides and hydrogen cyanide is in the range of 1.2 mole to 3.0 mole with respect to 1 mole of the benzaldehyde compound represented by formula (1).

[15] The process according to any one of [10] to [14], wherein Q is an optionally substituted phenyl group, X is a hydrogen atom, M is an oxy group (—O—) and n is 1 in formulae (1) and (2).

Effect of the Invention

The present invention can provide a process which is capable of producing a mandelonitrile compound in good yield.

MODES FOR CARRYING OUT THE INVENTION

The present invention will be illustrated in detail below. The present invention is a process for producing a mandelonitrile compound represented by formula (2) (hereinafter referred to as "compound (2)" in some cases), comprising a step of reacting a benzaldehyde compound represented by formula (1) (hereinafter referred to as "compound (1)" in some cases) with at least one member selected from the group consisting of metal cyanides and hydrogen cyanide (hereinafter referred to as "cyanating agent" in some cases) in the presence of a phase transfer catalyst in a solvent (hereinafter referred to as "present reaction" in some cases).

The hydrocarbon group having 1 to 14 carbon atoms in the optionally substituted hydrocarbon group having 1 to 14 carbon atoms represented by Q in the formulae (1) and (2) includes, for example, aryl groups having 6 to 14 carbon atoms, alkyl groups having 1 to 14 carbon atoms, alkenyl groups having 2 to 14 carbon atoms and alkynyl groups having 2 to 14 carbon atoms.

The aryl group having 6 to 14 carbon atoms includes, for example, a phenyl group, a 1-naphthyl group and a 2-naphthyl group, and the aryl group having 6 to 14 carbon atoms may have at a substitutable position, for example, 1 to 5 substituents, preferably 1 to 4 substituents, more preferably 1 to 3 substituents inert to the present reaction. When a plurality of substituents are present, these substituents are independent of one another, and may be mutually the same or different. The substituent optionally carried on the aryl group having 6 to 14 carbon atoms includes, for example, at least one group selected from the following Group P1.

In the following descriptions, lower means that the number of carbon atoms contained in its group is 1 to 8, and preferably, the number of carbon atoms contained in its group is 6 or less, more preferably, the number of carbon atoms contained in its group is 4 or less.

Group P1:

Lower alkyl groups such as a methyl group, an ethyl group, a propyl group, an isopropyl group, a butyl group, an isobutyl group, a t-butyl group, a pentyl group and a hexyl group; lower alkenyl groups such as an ethenyl group, a 2-propenyl group and a crotyl group; lower alkynyl groups such as an ethynyl group, a propargyl group and a butynyl group; lower cycloalkyl groups such as a cyclopropyl group, a cyclopentyl group and a cyclohexyl group; lower alkyl groups having a lower alkoxy group such as a methoxymethyl group, an ethoxymethyl group and a 2-methoxyethyl group; lower cycloalkenyl groups such as a cyclopentenyl group and a cyclohexenyl group; lower alkanoyl groups such as an acetyl group, a propionyl group and an isobutyryl group; tri-lower alkylsilyl groups such as a trimethylsilyl group, a triethylsilyl group, a tripropylsilyl group and a tributylsilyl group; halo-lower alkyl groups such as a difluoromethyl group, a trifluoromethyl group, a chloromethyl group, a 2-bromoethyl group and a 2,3-dichloropropyl; di-lower alkylamino groups such as a dimethylamino group and a diethylamino group; a phenyl group; lower alkyl groups having a phenyl group such as a benzyl group and a phenethyl group; lower alkenyl groups having a phenyl group such as a styryl group and a cinnamyl group; lower alkyl groups having a furyl group such as a 3-furylmethyl group and a 2-furylethyl group; lower alkenyl groups having a furyl group such as a 3-furylvinyl group and a 2-furylallyl group; halogen atoms such as a fluorine atom, a chlorine atom, a bromine atom and an iodine atom; a nitro group; a cyano group; lower alkylthio groups such as a methylthio group, an ethylthio group, a propylthio group and a butylthio group; lower alkoxycarbonyl groups such as a methoxycarbonyl group, an ethoxycarbonyl group and a propoxycarbonyl group; a formyl group; amino groups optionally protected by a formyl group and the like; mono-lower alkylamino groups such as a methylamino group and an ethylamino group; amino groups mono-substituted with a lower alkylcarbonyl group such as a methylcarbonylamino group; groups represented by —OR (R represents a hydrogen atom or a group selected from the following Group 22) and —CH$_2$-G-R' [G represents an oxy group (—O—), a thio group (—S—) or —NR"— (here, R" represents a hydrogen atom or a lower alkyl group) and R' represents a phenyl group; a halophenyl group such as a 2-chlorophenyl group and a 4-fluorophenyl group; a lower alkoxyphenyl group such as a 2-methoxyphenyl group and a 4-ethoxyphenyl group; a pyridyl group or a pyrimidinyl group.].

Group P2:

Lower alkyl groups such as a methyl group, an ethyl group, a propyl group and a butyl group; lower alkenyl groups such as an ethenyl group, a 2-propenyl group and a crotyl group; lower alkynyl groups such as an ethynyl group, a 2-propynyl group and a 3-butynyl group; halo-lower alkyl groups such as a difluoromethyl group, a trifluoromethyl group, a chloromethyl group, a 2-bromoethyl group and a 2,3-dichloropropyl group; lower alkanoyl groups such as an acetyl group, a propionyl group and a butyryl group; aryl groups such as a phenyl group; lower alkoxyphenyl groups such as a 3-methoxyphenyl and a 4-ethoxyphenyl; nitrophenyl groups such as a 3-nitrophenyl group and a 4-nitrophenyl group; lower alkyl groups having a phenyl group such as a benzyl group, a phenethyl group and a phenylpropyl group; lower alkyl groups having a cyanophenyl group such as a 3-cyanophenylmethyl group and a 4-cyanophenylethyl group; a benzoyl group; a tetrahydropyranyl group; a pyridyl group; a trifluoromethylpyridyl group; a pyrimidinyl group; a benzothiazolyl group; a quinolyl group; lower alkyl groups having a benzoyl group such as a benzoylmethyl group and a benzoylethyl group; and benzenesulfonyl groups having a lower alkyl group such as a benzenesulfonyl group and a toluenesulfonyl group.

The optionally substituted aryl group having 6 to 14 carbon atoms is preferably an optionally substituted phenyl group, more preferably a group represented by formula (3):

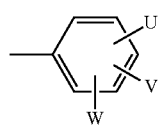

(3)

wherein U, V and W are independently a hydrogen atom or a group selected from the above-described Group P1. In formula (3), U, V and W are independently, preferably, a hydrogen atom, a halogen atom, a lower alkyl group, a halo-lower alkyl group, a lower alkyl group having a lower alkoxy group, a group represented by —OR, a lower alkylthio group, an optionally protected amino group or a mono-lower alkylamino group or a di-lower alkylamino group.

U, V and W are independently, preferably, a hydrogen atom, a chlorine atom, a methyl group, an ethyl group, a trifluoromethyl group, a methoxy group, a methylthio group or a dimethylamino group, more preferably, a hydrogen atom, a chlorine atom, a methyl group or a methoxy group.

The alkyl group having 1 to 14 carbon atoms in the optionally substituted hydrocarbon group having 1 to 14 carbon atoms represented by Q includes, for example, a methyl group, an ethyl group, a propyl group, an isopropyl group, a butyl group, an isobutyl group, a t-butyl group, a pentyl group, a hexyl group, a heptyl group, an octyl group, a nonyl group and a decyl group, and preferable are alkyl groups having 1 to 8 carbon atoms, more preferable are alkyl groups having 1 to 4 carbon atoms.

The alkenyl group having 2 to 14 carbon atoms in the optionally substituted hydrocarbon group having 1 to 14 carbon atoms represented by Q includes, for example, an ethenyl group, a 1-propenyl group, a 2-propenyl group, an isopropenyl group, a 1-butenyl group, a 2-butenyl group, an isobutenyl group, a 1-pentenyl group, a 2-pentenyl group, a 1-hexenyl group, a 2-hexenyl group, a 1,3-hexadienyl group, a 2,4-hexadienyl group and a 3,5-hexadienyl group, and preferable are alkenyl groups having 2 to 8 carbon atoms, more preferable are alkenyl groups having 3 to 6 carbon atoms.

The alkynyl group having 2 to 14 carbon atoms in the optionally substituted hydrocarbon group having 1 to 14 carbon atoms represented by Q includes, for example, an ethynyl group, a propargyl group, a 1-butynyl group, a 2-butynyl group and a 3-butynyl group, and preferable are alkynyl groups having 2 to 6 carbon atoms, more preferable are alkynyl groups having 2 to 4 carbon atoms.

The alkyl group having 1 to 14 carbon atoms, the alkenyl group having 2 to 14 carbon atoms and the alkynyl group having 2 to 14 carbon atoms in the optionally substituted hydrocarbon group having 1 to 14 carbon atoms represented by Q may have at a substitutable position a substituent inert to the present reaction, and the substituent optionally carried on the alkyl group, the alkenyl group and the alkynyl group includes, for example, the halogen atoms, the lower alkylthio groups and the optionally protected amino groups exemplified for U, V and W, and for example, lower alkylsulfinyl groups and lower alkylsulfonyl groups for $R^4$ and $R^5$ described later, and for example, the optionally substituted aryl groups having 6 to 14 carbon atoms exemplified for Q, and for example, optionally substituted heterocyclic groups having 3 to 12 carbon atoms described later, further for example, alkoxy groups having 1 to 8 carbon atoms such as a methoxy group, an ethoxy group, a propoxy group, an isopropoxy group, a butoxy group, an isobutoxy group, a t-butoxy group, a pentyloxy group and a hexyloxy group (the carbon atom number of the alkoxy group is preferably 1 to 4), haloalkoxy groups having a halogen atom such as a fluorine atom, a chlorine atom, a bromine atom and an iodine atom (the halogen atom is preferably a fluorine atom) (specifically, a difluoromethoxy group, a trifluoromethoxy group, a chloromethoxy group and the like), alkoxyalkoxy groups having an alkoxy group having 1 to 8 carbon atoms such as a methoxy group, an ethoxy group, a propoxy group and a butoxy group (the carbon atom number of the alkoxy group is preferably 1 to 4) (specifically, a methoxymethoxy group, a 2-methoxyethoxy group, an ethoxymethoxy group and the like); and groups represented by formula (5):

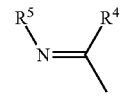

(5)

wherein $R^4$ and $R^5$ represent independently a hydrogen atom, an optionally substituted lower alkyl group, an acyl group, a lower alkylthio group, a lower alkylsulfinyl group, a lower alkylsulfonyl group, an optionally protected amino group, a cycloalkyl group, an optionally substituted aryl group or an optionally substituted heterocyclic group, alternatively, $R^4$ and $R^5$ are linked to form a single- or poly-ring optionally containing a hetero atom.

The optionally substituted lower alkyl group represented by $R^4$ or $R^5$ includes, for example, the same groups as the lower alkyl group, the halo-lower alkyl group and the lower alkyl group having a lower alkoxy group exemplified for U, V and W, and a methyl group or an ethyl group is preferable. The acyl group represented by $R^4$ or $R^5$ includes, for example, lower alkylcarbonyl groups and arylcarbonyl groups. The lower alkylcarbonyl group includes, for example, an acetyl group, a trifluoroacetyl group, a propionyl group and a butyryl group. The arylcarbonyl group includes, for example, arylcarbonyl groups having 7 to 15 carbon atoms such as a benzoyl group and a naphthoyl group.

The lower alkylthio group and the optionally protected amino group represented by $R^4$ or $R^5$ include, respectively, the same groups as the lower alkylthio group and the same groups as the optionally protected amino group exemplified for U, V and W.

The lower alkylsulfinyl group represented by $R^4$ or $R^5$ includes, for example, a methylsulfinyl group, an ethylsulfinyl group and a propylsulfinyl group, and preferable is a methylsulfinyl group.

The lower alkylsulfonyl group represented by $R^4$ or $R^5$ includes, for example, a methylsulfonyl group, an ethylsulfonyl group, a propylsulfonyl group and the like, and preferable is a methylsulfonyl group.

The cycloalkyl group represented by $R^4$ or $R^5$ includes, for example, cycloalkyl groups having 3 to 7 carbon atoms such as a cyclopropyl group, a cyclobutyl group, a cyclopentyl group, a cyclohexyl group and a cycloheptyl group, preferably, cycloalkyl groups having 5 to 6 carbon atoms.

The optionally substituted aryl group represented by $R^4$ or $R^5$ includes, for example, aryl groups having 6 to 14 carbon atoms such as a phenyl group, a naphthyl group (for example, a 1-naphthyl group) and a fluorenyl group, and preferable is a phenyl group. The aryl group may have, at a substitutable position, for example, 1 to 3 substituents. The substituent optionally carried on the aryl group includes a halogen atom, an optionally substituted lower alkyl group, a group represented by —OR (R are each as described above), a lower alkylthio group, an optionally protected amino group, a nitro group, a phenyl group and a cyano group.

The halogen atom as the substituent optionally carried on the aryl group represented by $R^4$ or $R^5$ includes, for example, a fluorine atom, a chlorine atom, a bromine atom and an iodine atom. The optionally substituted lower alkyl group includes the same groups as the lower alkyl group, the halolower alkyl group and the lower alkyl group having a lower alkoxy group exemplified for U, V and W, and preferable are lower alkyl groups or halo-lower alkyl groups, more preferable is a methyl group or a trifluoromethyl group. The group represented by —OR includes lower alkoxy groups such as a methoxy group, an ethoxy group, a propoxy group and a butoxy group; lower alkenyloxy groups such as a vinyloxy group, an allyloxy group and a crotyloxy group; lower alkynyloxy groups such as an ethynyloxy group, a propargyloxy group and a butynyloxy group; halo-lower alkoxy groups such as a difluoromethoxy group, a trifluoromethoxy group and a chloromethoxy group; and aryloxy groups such as a phenoxy group and a naphthoxy group, and preferable is a methoxy group, an allyloxy group, a propargyloxy group or a difluoromethoxy group. The lower alkylthio group includes, for example, a methylthio group, an ethylthio group, a propylthio group and a butylthio group, and preferable is a methylthio group or an ethylthio group, more preferable is a methylthio group. The optionally protected amino group includes, for example, an amino group; mono-lower alkylamino groups such as a methylamino group and an ethylamino group; and di-lower alkylamino groups such as a dimethylamino group.

The optionally substituted heterocyclic group represented by $R^4$ or $R^5$ includes heterocyclic groups containing in its ring, for example, 1 to 4, preferably, 1 to 2 hetero atoms (for example, an oxygen atom, a nitrogen atom, a sulfur atom), and examples thereof include a pyridyl group, a pyridazinyl group, a pyrazolyl group, a pyrimidinyl group, a furyl group, a thienyl group, an oxazolyl group, an isooxazolyl group, a benzothiazolyl group, a quinolyl group, a quinazolinyl group, a pyrazinyl group, a morpholino group and a piperazinyl group. The heterocyclic group is, preferably, a furyl group (for example, a 2-furyl group), a thienyl group (for example, a 2-thienyl group), a pyridyl group (for example, a 2-pyridyl group), a pyrazinyl group (for example, a 2-pyrazinyl group), a pyrimidinyl group (for example, a 2-pyrimidinyl group) or a morpholino group. The heterocyclic group may have at a substitutable position a substituent, and this substituent includes the same groups as the substituent optionally carried on the aryl group represented by $R^4$ or $R^5$.

The single- or poly-ring optionally containing a hetero atom formed by linking of $R^4$ and $R^5$ is a 4 to 8-membered ring optionally containing a hetero atom (for example, an oxygen atom, a nitrogen atom, a sulfur atom) formed of $R^4$ and $R^5$ together with a carbon atom and a nitrogen atom to which $R^4$ and $R^5$ are linked, and this ring may form a condensed ring. The single- or poly-ring includes, for example, a cyclopentane ring, a cyclohexane ring, an indane ring, a 1,2, 3,4-tetrahydronaphthalene ring, a 5,6,7,8-tetrahydroquinoline ring and a 4, 5, 6, 7-tetrahydrobenzo[b]furan ring.

The heterocyclic group having 3 to 12 carbon atoms in the optionally substituted heterocyclic group having 3 to 12 carbon atoms represented by Q includes, for example, 5 to 7-membered heterocyclic groups containing 1 to 4 hetero atoms selected from the group consisting of a nitrogen atom, an oxygen atom and a sulfur atom as a ring constituent atom. These heterocyclic groups may further form a condensed ring together with another hetero ring or a benzene ring. The heterocyclic group having 3 to carbon atoms includes, for example, pyridyl groups such as a pyridin-2-yl group and a pyridin-3-yl group; pyrimidinyl groups such as a pyrimidin-4-yl group and a pyrimidin-2-yl group; quinolyl groups such as a quinolin-4-yl group; quinazolinyl groups such as a quinazolin-4-yl group; benzothiazolyl groups such as a benzothiazol-2-yl group; and pyrazolyl groups such as a pyrazol-5-yl group, and preferable is a pyridyl group. The heterocyclic group having 3 to 12 carbon atoms may have at a substitutable position, for example, 1 to substituents, preferably 1 to 4 substituents, more preferably 1 to 3 substituents inert to the present reaction. When a plurality of substituents are present, these substituents are independent of one another, and may be mutually the same or different.

The optionally substituted methyleneamino group represented by Q is, for example, a group represented by formula (4):

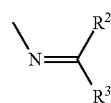

(4)

wherein $R^2$ and $R^3$ represent independently a hydrogen atom, an optionally substituted lower alkyl group, an acyl group, a lower alkylthio group, a lower alkylsulfinyl group, a lower alkylsulfonyl group, an optionally protected amino group, a lower cycloalkyl group, an optionally substituted aryl group or an optionally substituted heterocyclic group, alternatively, $R^2$ and $R^3$ are linked to form a single- or poly-ring optionally containing a hetero atom. The optionally substituted lower alkyl group, the acyl group, the lower alkylthio group, the lower alkylsulfinyl group, the lower alkylsulfonyl group, the optionally protected amino group, the lower cycloalkyl group, the optionally substituted aryl group or the optionally substituted heterocyclic group represented by $R^2$ or $R^3$ and the single- or poly-ring optionally containing a hetero atom formed by linking of $R^2$ and $R^3$ include, respectively, the same groups as the optionally substituted lower alkyl group, the acyl group, the lower alkylthio group, the lower alkylsulfinyl group, the lower alkylsulfonyl group, the optionally protected amino group, the lower cycloalkyl group, the optionally substituted aryl group or the optionally substituted heterocyclic group represented by $R^4$ or $R^5$ and the single- or poly-ring optionally containing a hetero atom formed by linking of $R^2$ and $R^3$ described above.

The optionally substituted acyl group having 2 to 15 carbon atoms represented by Q includes, for example, optionally substituted alkylcarbonyl groups, optionally substituted phenylcarbonyl groups, optionally substituted naphthylcarbonyl groups and carbonyl groups having an optionally substituted heterocyclic group. The optionally substituted alkyl (group) in such an acyl group includes the same groups as the lower alkyl group, the halo-lower alkyl group and the lower alkyl group having a lower alkoxy group exemplified for U, V and W, and the optionally substituted phenyl (group), the optionally substituted naphthyl (group) and the optionally substituted heterocyclic group include, respectively, the same groups as the groups exemplified for Q.

The optionally substituted substituted-sulfonyl group having 1 to 14 carbon atoms represented by Q includes, for example, optionally substituted alkylsulfonyl groups, optionally substituted phenylsulfonyl groups, optionally substituted naphthylsulfonyl groups and sulfonyl groups having an optionally substituted heterocyclic group. The optionally substituted alkyl (group) in such a substituted-sulfonyl group includes the same groups as the lower alkyl group, the halo-lower alkyl group and the lower alkyl group having a lower alkoxy group exemplified for U, V and W, and the optionally substituted phenyl (group), the optionally substituted naphthyl (group) and the optionally substituted heterocyclic group include, respectively, the same groups as the groups exemplified for Q.

Q is, preferably, a group represented by formula (3), an optionally substituted pyridyl group, an optionally substituted pyrimidinyl group, an optionally substituted quinolyl group, an optionally substituted quinazolinyl group, an optionally substituted benzothiazolyl group, an optionally substituted pyrazolyl group or a group represented by formula (4).

X represents a hydrogen atom, a halogen atom, an optionally substituted alkyl group having 1 to 8 carbon atoms or an optionally protected hydroxyl group, and when there are a plurality of Xs, these may be the same or different. The halogen atom represented by X includes, for example, the same atoms as the halogen atom exemplified in Group P1, the optionally substituted alkyl group having 1 to carbon atoms includes, for example, the same groups as the lower alkyl group, the halo-lower alkyl group and the lower alkyl group having a lower alkoxy group exemplified for U, V and W, the optionally protected hydroxyl group includes the same groups as the group represented by —OR described above, and X is, preferably, a hydrogen atom.

The alkyl group having 1 to 8 carbon atoms represented by R includes, for example, the same groups as the lower alkyl group exemplified for U, V and W, and preferable is a methyl group. The acyl group having 1 to 9 carbon atoms represented by $R^1$ includes, for example, a formyl group; carbonyl groups having a lower alkyl group such as an acetyl group, a propionyl group and a butyryl group; and a benzoyl group, and preferable is an acetyl group.

M is preferably an oxy group (—O—), a thio group (—S—) or —NR—, more preferably an oxy group (—O—).

n is preferably 0 or 1, more preferably 1.

The compound (1) is preferably a compound in which Q is an optionally substituted phenyl group or an optionally substituted heterocyclic group, X is a hydrogen atom, M is an oxy group (—O—) and n is 0 or 1; or a compound in which Q is a group represented by formula (3) ($R^2$ is a lower alkyl group, $R^3$ is an optionally substituted phenyl group or an optionally substituted morpholino group), X is a hydrogen atom, M is an acylamino group and n is 1, more preferably a compound in which Q is an optionally substituted phenyl group, X is a hydrogen atom, M is an oxy group (—O—) and n is 1.

Preferable examples of the compound (1) include, specifically, a compound in which Q is a phenyl group, X is a hydrogen atom, M is an oxy group (—O—) and n is 0; a compound in which Q is a 3,4-dimethylphenyl group, X is a hydrogen atom, M is an oxy group (—O—) and n is 0; a compound in which Q is a 3,5-dimethylphenyl group, X is a hydrogen atom, M is an oxy group (—O—) and n is 0; a compound in which Q is a 2-methylphenyl group, X is a hydrogen atom, M is an oxy group (—O—) and n is 1; a compound in which Q is a 2,5-dimethylphenyl group, X is a hydrogen atom, M is an oxy group (—O—) and n is 1; a compound in which Q is a 4-chloro-2-methylphenyl group, X is a hydrogen atom, M is an oxy group (—O—) and n is 1; a compound in which Q is a 2,5-dimethylphenyl group, X is a hydrogen atom, M is an oxy group (—O—) and n is 1; a compound in which Q is a 3-chloro-5-trifluoromethylpyridin-2-yl group, X is a hydrogen atom, M is an oxy group (—O—) and n is 1; a compound in which Q is a 3,5-dichloropyridin-2-yl group, X is a hydrogen atom, M is an oxy group (—O—) and n is 1; a compound in which Q is a 3-trifluoromethyl-5-chloropyridin-2-yl group, X is a hydrogen atom, M is an oxy group (—O—) and n is 1; a compound in which Q is a 3-chloropyridin-2-yl group, X is a hydrogen atom, M is an oxy group (—O—) and n is 1; a compound in which Q is an α-methyl-4-chlorobenzylideneamino group, X is a hydrogen atom, M is an oxy group (—O—) and n is 1; a compound in which Q is an α-methyl-4-methoxybenzylideneamino group, X is a hydrogen atom, M is an oxy group (—O—) and n is 1; a compound in which Q is a 4,α-dimethylbenzylideneamino group, X is a hydrogen atom, M is an oxy group (—O—) and n is 1; and a compound in which Q is an α-methyl-4-trifluoromethylbenzylideneamino group, X is a hydrogen atom, M is an oxy group (—O—) and n is 1, and more further preferable is a compound in which Q is a 2,5-dimethylphenyl group, X is a hydrogen atom, M is an oxy group (—O—) and n is 1.

The cyanating agent used in the present reaction includes, for example, sodium cyanide, potassium cyanide and hydrogen cyanide. The cyanating agent can be dissolved in water and used, or can be dissolved in an alcohol such as methanol and used. The use amount of the cyanating agent is preferably in the range of 1.2 mole to 3.0 mole, more preferably in the range of 1.5 mole to 2.0 mole with respect to 1 mole of the compound (1). When the use amount of the cyanide is over 3.0 mole, the unreacted cyanating agent tends to remain in larger amount.

The phase transfer catalyst used in the present reaction includes, for example, quaternary ammonium salts such as tetra-n-butylammonium bromide (hereinafter referred to as "TBAB" in some cases), benzyltriethylammonium chloride and methyltributylammonium chloride; quaternary phosphonium salts such as tetra-n-butyl phosphonium chloride; and crown ethers such as 15-crown-5, 18-crown-6, and preferable are quaternary ammonium salts, more preferable is tetra-n- butylammonium bromide or methyltributylammonium chloride. As necessary, two or more phase transfer catalysts can be used. The use amount of the phase transfer catalyst is, for example, in the range of 0.001 mole to 1 mol, preferably, in the range of 0.01 mole to 0.1 mole with respect to 1 mole of the benz compound (1). When the present reaction is carried out in the absence of the phase transfer catalyst, a compound (1) having a prescribed substituent at an ortho position shows low reactivity and sufficient conversion ratio tends not to be obtained.

The present reaction is carried out in a solvent, and carried out, for example, in an organic solvent or in a mixed solvent composed of an organic solvent and water. Examples of the organic solvent include alcohols such as methanol, ethanol, isopropanol, 1-propanol, ethylene glycol and 1-butanol (the carbon atom number of the alcohol is preferably 1 to 4); ethers such as diethyl ether, dibutyl ether, methyl tert-butyl ether, tetrahydrofuran and tetrahydropyran; ester such as ethyl acetate, butyl acetate and ethyl butyrate; halogenated hydrocarbons such as dichloromethane, chloroform and carbon tetrachloride; aromatic hydrocarbons such as benzene, toluene, xylene and chlorobenzene; aliphatic hydrocarbons such as n-hexane and n-heptane; and alicyclic hydrocarbons such as cyclopentane and cyclohexane. The solvent is preferably one containing a highly polar organic solvent such as an alcohol, an ether and an ester, more preferably one containing an alcohol, from the viewpoint of improvement of the yield of a compound (2). It is preferable to use as the solvent at least one member selected from the group consisting of aromatic hydrocarbons, aliphatic hydrocarbons and halogenated hydrocarbons (hereinafter referred to as "low-polar solvent" in some cases) and water, from the viewpoint of easiness of removal of a cyanating agent after completion of the present reaction. The present reaction is preferably carried out in a solvent containing an alcohol, more preferably carried out in a mixed solvent composed of water, an alcohol and at least one solvent selected from the group consisting of aromatic hydrocarbons, aliphatic hydrocarbons and halogenated hydrocarbons.

The use amount of the organic solvent is, for example, in the range of 0.5 parts by weight to 10 parts by weight, preferably, in the range of 1 part by weight to 5 parts by weight with respect to 1 part by weight of the compound (1). The use amount of the water is, for example, in the range of 0.3 parts by weight to 5 parts by weight, preferably, in the range of 0.5 parts by weight to 2 parts by weight with respect to 1 part by weight of the compound (1).

When water is used in the present reaction, it is preferable to adjust the pH of a solvent during the present reaction, and for improving the yield of a compound (2), the solvent is more preferably adjusted to pH 5 to 9, further preferably adjusted to pH 6 to 8, more further preferably adjusted to pH 7.2 to 7.6. As the method of adjusting the pH of a solvent during the present reaction in such a case using water, there is, for example, a method of adjusting the pH of a mixed liquid during the present reaction in which the pH of an aqueous layer in the mixed liquid during the present reaction is measured, and if the measured value is larger than desired pH, then, an acid is added and if the measured value is smaller than desired pH, then, a base is added. More details are as described below.

The pH of a solvent during the present reaction is adjusted, for example, by adding an acid and/or a base. The acid includes, for example, organic acids such as formic acid, acetic acid, butyric acid, citric acid, methanesulfonic acid and p-toluenesulfonic acid; inorganic acids such as hydrochloric acid (aqueous solution of hydrogen chloride), sulfuric acid, phosphoric acid, sodium bisulfate and ammonium chloride. As necessary, two or more acids can be used. As the acid, preferable are organic acids having low acidity, more preferable is acetic acid, because of easiness of adjustment of pH. The use amount of the acid is in the range of about 1 mole to about 1.1 mole with respect to 1 mole of the cyanating agent, and it is preferable to use the amount generating the above-described prescribed pH. The base includes, for example, sodium hydroxide and sodium bicarbonate. The base is used when the pH of water in the present reaction is, for example, less than 5, or for example, less than 6, or for example, less than 7.

The present reaction can be carried out, for example, by the following methods (a) to (d).

(a) A method in which an aqueous solution of a cyanating agent is added to a mixture of an organic solvent, water, a phase transfer catalyst and a compound (1), and an acid is added or dropped in one lump thereto;

(b) A method in which an aqueous solution of a cyanating agent and an acid are concurrently added to a mixture of an organic solvent, water, a phase transfer catalyst and a compound (1);

(c) A method in which an acid is added to a mixture of an organic solvent, water, a phase transfer catalyst and a compound (1), and an aqueous solution of a cyanating agent is added or dropped in one lump thereto;

(d) A method in which a compound (1) dissolved in an organic solvent is added to a mixture of a phase transfer catalyst, an acid and an aqueous solution of a cyanating agent.

The present reaction is preferably carried out by the method described in (a) or the method described in (b), for adjusting the pH of water during the present reaction in a preferable range. In the case of dropping of an aqueous solution of a cyanating agent and/or an acid, the dropping time is, for example, in the range of 0.5 hours to 20 hours, preferably, in the range of 1 hour to 10 hours.

The reaction temperature of the present reaction is selected, for example, in the range of −20° C. to 50° C., preferably, in the range of 0° C. to 30° C. In the present reaction, a compound (1), a cyanating agent and, as necessary an acid, are mixed, then, the mixture is stirred while keeping warm for preferably in the range of 0.5 hours to 20 hours, more preferably in the range of 1 hour to 10 hours.

After completion of the present reaction, a compound (2) can be obtained in good yield. As necessary, a compound (2) may be purified, and for example, a compound (2) can be purified by adding acidic water such as hydrochloric acid (aqueous solution of hydrogen chloride) and sulfuric acid aqueous solution to the reaction mixture obtained in the present reaction, then, separating an oil and water, and removing a solvent and the like from the resultant oil layer. In this procedure, it is preferable to add a stabilizer such as p-toluenesulfonic acid and 2-ethylhexyl phosphate into the oil layer.

Further, it is also possible to crystallize a compound (2) by separating an oil and water, then, adding an aromatic hydrocarbon such as benzene, toluene, xylene and chlorobenzene; an aliphatic hydrocarbon such as n-hexane and n-heptane; an alicyclic hydrocarbon such as cyclopentane and cyclohexane, as a poor solvent, or by separating an oil and water, then, performing a cooling operation, and the like.

EXAMPLES

The present invention will be illustrated further in detail by examples below. In the following examples, the reaction mixture was analyzed by high performance liquid chromatography to determine the amounts of a compound (1) and a compound (2) contained in the reaction mixture, and the conversion ratio and the residual ratio of the compound (1) and the yield of the compound (2) were calculated.

Example 1

Into a 200 mL flask were charged 10.02 g of 2-(2,5-dimethylphenoxymethyl)benzaldehyde (content: 94.6% by weight, 0.039 mole), 20.05 g of xylene, 14.26 g of methanol, 3.87 g of water and 0.26 g of TBAB (content: 98.0% by weight, 0.0008 mole), and these were mixed, then, cooled to 10° C. while stirring. Subsequently, to the mixture was added an aqueous solution prepared by dissolving 2.98 g of sodium cyanide (content: 97.0% by weight, 0.059 mole (1.5 mole with respect to 1 mole of 2-(2,5-dimethylphenoxymethyl)benzaldehyde)) in 8.70 g of water, and an aqueous solution prepared by dissolving 3.68 g of acetic acid (content: 99.7% by weight, 0.061 mole) in 0.42 g of water was dropped over a period of 0.5 hours. After dropping, the aqueous layer showed pH 7.76, and 0.26 g of acetic acid was added to adjust pH to 7.37. After pH adjustment, the reaction mixture was stirred at 10° C. for 3 hours. This reaction mixture was analyzed to find that the conversion ratio of 2-(2,5-dimethylphenoxymethyl)benzaldehyde was 95.9% and the residual ratio thereof was 4.1%, and the yield of 2-(2,5-dimethylphenoxymethyl)mandelonitrile was 95.9%.

Example 2

Into a 200 mL flask were charged 20.03 g of 2-(2,5-dimethylphenoxymethyl)benzaldehyde (content: 94.6% by weight, 0.079 mole), 40.01 g of xylene, 28.38 g of methanol, 7.01 g of water and 0.52 g of TBAB (content: 98.0% by weight, 0.002 mole), and these were mixed, then, cooled to 10° C. while stirring. Subsequently, to the mixture was added an aqueous solution prepared by dissolving 5.58 g of sodium cyanide (content: 97.0% by weight, 0.11 mole (1.4 mole with respect to 1 mole of 2-(2,5-dimethylphenoxymethyl)benzaldehyde)) in 16.25 g of water, and an aqueous solution prepared by dissolving 6.89 g of acetic acid (content: 99.7% by weight, 0.11 mole) in 0.77 g of water was dropped over a period of 0.5 hours. After dropping, the aqueous layer showed pH 7.86, and 0.43 g of acetic acid was added to adjust pH to 7.38. After pH adjustment, the reaction mixture was stirred at 10° C. for 3 hours. This reaction mixture was analyzed to find that the conversion ratio of 2-(2,5-dimethylphenoxymethyl)benzaidehyde was 95.6% and the residual ratio thereof was 4.4%, and the yield of 2-(2,5-dimethylphenoxymethyl)mandelonitrile was 95.6%.

Example 3

Into a 200 mL flask were charged 10.03 g of 2-(2,5-dimethylphenoxymethyl)benzaidehyde (content: 98.2% by weight, 0.040 mole), 20.64 g of xylene, 14.83 g of methanol and 0.22 g of benzyltriethylammonium chloride (content: 98.0% by weight, 0.001 mole), and these were mixed, then, cooled to 10° C. while stirring. Subsequently, an aqueous solution prepared by dissolving 3.11 g of sodium cyanide (content: 97.0% by weight, 0.062 mole (1.5 mole with respect to 1 mole of 2-(2,5-dimethylphenoxymethyl)benzaldehyde)) in 9.06 g of water and an aqueous solution prepared by dissolving 3.84 g of acetic acid (content: 99.7% by weight, 0.064 mole) in 4.42 g of water were dropped concurrently into the mixture while keeping pH 6 to 8 over a period of 0.5 hours. After dropping, the aqueous layer showed pH 7.61, and 0.25 g of acetic acid was added to adjust pH to 7.12. After pH adjustment, the reaction mixture was stirred at 10° C. for 7 hours. This reaction mixture was analyzed to find that the conversion ratio of 2-(2,5-dimethylphenoxymethyl)benzaldehyde was 96.4% and the residual ratio thereof was 3.6%, and the yield of 2-(2,5-dimethylphenoxymethyl)mandelonitrile was 96.4%.

Example 4

Into a 200 mL flask were charged 20.03 g of 2-(2,5-dimethylphenoxymethyl)benzaldehyde (content: 94.6% by weight, 0.079 mole), 39.78 g of xylene, 28.38 g of methanol, 7.70 g of water and 0.50 g of Aliquat (registered trademark) 175 (content: 75% by weight, 0.002 mole), and these were mixed, then, cooled to 10° C. while stirring. Subsequently, to the mixture was added an aqueous solution prepared by dissolving 5.97 g of sodium cyanide (content: 97.0% by weight, 0.12 mole (1.5 mole with respect to 1 mole of 2-(2,5-dimethylphenoxymethyl)benzaldehyde)) in 17.40 g of water, and an aqueous solution prepared by dissolving 7.37 g of acetic acid (content: 99.7% by weight, 0.12 mole) in 0.83 g of water was dropped over a period of 0.5 hours. After dropping, the aqueous layer showed pH 7.96, and 0.60 g of acetic acid was added to adjust pH to 7.39. After pH adjustment, the reaction mixture was stirred at 10° C. for 4 hours. This reaction mixture was analyzed to find that the conversion ratio of 2-(2,5-dimethylphenoxymethyl)benzaldehyde was 96.2% and the residual ratio thereof was 3.8%, and the yield of 2-(2,5-dimethylphenoxymethyl)mandelonitrile was 96.2%.

Example 5

Into a 200 mL flask were charged 10.01 g of 2-(2,5-dimethylphenoxymethyl)benzaldehyde (content: 94.6% by weight, 0.039 mole), 20.00 g of xylene, 14.18 g of methanol, 3.08 g of water and 0.26 g of TBAD (content: 98.0% by weight, 0.0008 mole), and these were mixed, then, cooled to 10° C. while stirring. Subsequently, to the mixture was added an aqueous solution prepared by dissolving 2.40 g of sodium cyanide (content: 97.0% by weight, 0.048 mole (1.2 mole with respect to 1 mole of 2-(2,5-dimethylphenoxymethyl)benzaldehyde)) in 7.00 g of water, and an aqueous solution prepared by dissolving 2.96 g of acetic acid (content: 99.7% by weight, 0.049 mole) in 0.34 g of water was dropped over a period of 0.5 hours. After dropping, the aqueous layer showed pH 7.39, and the reaction mixture was stirred at 10° C. for 7 hours. This reaction mixture was analyzed to find that the conversion ratio of 2-(2,5-dimethylphenoxymethyl)benzaldehyde was 92.4% and the residual ratio thereof was 7.6%, and the yield of 2-(2,5-dimethylphenoxymethyl)mandelonitrile was 92.4%.

Example 6

Into a 200 mL flask were charged 10.01 g of 2-(2,5-dimethylphenoxymethyl)benzaldehyde (content: 98.2% by weight, 0.039 mole), 20.67 g of xylene, 15.00 g of methanol and 0.14 g of TBAB (content: 98.0% by weight, 0.0004 mole), and these were mixed, then, cooled to 10° C. while stirring. Subsequently, an aqueous solution prepared by dissolving 3.10 g of sodium cyanide (content: 97.0% by weight, 0.061 mole (1.5 mole with respect to 1 mole of 2-(2,5-dimethylphenoxymethyl)benzaldehyde)) in 9.08 g of water and an aqueous solution prepared by dissolving 3.82 g of acetic acid (content: 99.7% by weight, 0.063 mole) in 4.44 g of water were dropped concurrently into the mixture while keeping pH 6 to 8 over a period of 0.5 hours. After dropping, the aqueous layer showed pH 7.73, and 0.20 g of acetic acid was added to adjust pH to 7.20. After pH adjustment, the reaction mixture was stirred at 10° C. for 6 hours. This reaction mixture was analyzed to find that the conversion ratio of 2-(2,5-dimethylphenoxymethyl)benzaldehyde was 95.6% and the residual ratio thereof was 4.4%, and the yield of 2-(2,5-dimethylphenoxymethyl)mandelonitrile was 95.6%.

Comparative Example 1

Into a 200 mL flask were charged 15.00 g of 2-(2,5-dimethylphenoxymethyl)benzaldehyde (content: 94.6% by weight, 0.059 mole), 46.47 g of methyl tert-butyl ether and 5.81 g of water, and these were mixed, then, cooled to 10° C. while stirring. Subsequently, to the mixture was added an aqueous solution prepared by dissolving 4.47 g of sodium cyanide (content: 97.0% by weight, 0.089 mole (1.5 mole with respect to 1 mole of 2-(2,5-dimethylphenoxymethyl) benzaldehyde)) in 13.03 g of water, and an aqueous solution prepared by dissolving 5.53 g of acetic acid (content: 99.7% by weight, 0.092 mole) in 0.62 g of water was dropped over a period of 0.5 hours. After dropping, the aqueous layer showed pH 7.73, and 0.16 g of acetic acid was added to adjust pH to 7.39. After pH adjustment, the reaction mixture was stirred at 10° C. for 4 hours. This reaction mixture was analyzed to find that the conversion ratio of 2-(2,5-dimethylphenoxymethyl) benzaldehyde was 40.2% and the residual ratio thereof was 59.8%, and the yield of 2-(2,5-dimethylphenoxymethyl)mandelonitrile was 40.2%.

Comparative Example 2

Into a 200 mL flask were charged 10.03 g of 2-(2,5-dimethylphenoxymethyl)benzaldehyde (content: 94.6% by weight, 0.040 mole) and 47.30 g of methanol, and these were mixed at room temperature. Subsequently, to the mixture was added 2.99 g of sodium cyanide (content: 97.0% by weight, 0.059 mole (1.5 mole with respect to 1 mole of 2-(2,5-dimethylphenoxymethyl)benzaldehyde)), and an aqueous solution prepared by dissolving 9.87 g (0.095 mole) of saturated sodium bisulfite in 23.50 g of water was dropped over a period of 0.5 hours. After dropping, the aqueous layer showed pH 7.03. The reaction mixture was stirred at room temperature for 7 hours, and this reaction mixture was analyzed to find that the conversion ratio of 2-(2,5-dimethylphenoxymethyl)benzaldehyde was 84.4% and the residual ratio thereof was 15.6%, and the yield of 2-(2,5-dimethylphenoxymethyl) mandelonitrile was 84.4%.

Example 7

Into a 200 mL flask was added an aqueous solution prepared by dissolving 5.57 g of sodium cyanide (content: 97.0% by weight, 0.11 mole (1.4 mole with respect to 1 mole of 2-(2,5-dimethylphenoxymethyl)benzaldehyde)) in 16.22 g of water, subsequently, 20.04 g of 2-(2,5-dimethylphenoxymethyl)benzaldehyde (content: 94.6% by weight, 0.079 mole), 39.86 g of xylene and 0.52 g of TEAR (content: 98.0% by weight, 0.002 mole) were charged and these were mixed at room temperature. Subsequently, 11.97 g of 35% hydrochloric acid (content: 35% by weight, 0.11 mole) was dropped over a period of 0.5 hours.

After dropping, pH was 0.33, and the conversion ratio of 2-(2,5-dimethylphenoxymethyl)benzaldehyde was 85.3% and the residual ratio thereof was 14.7% at this moment. Into the reaction system was added 0.56 g of a 27% sodium hydroxide aqueous solution to adjust pH to 7.19. After pH adjustment, the reaction mixture was stirred at room temperature for 7 hours.

This reaction mixture was analyzed to find that the conversion ratio of 2-(2,5-dimethylphenoxymethyl)benzaldehyde was 91.9% and the residual ratio thereof was 8.1%, and the yield of 2-(2,5-dimethylphenoxymethyl)mandelonitrile was 91.9%.

INDUSTRIAL APPLICABILITY

A mandelonitrile compound is, for example, useful as a production raw material or a production intermediate of medical and agricultural chemicals. Since a mandelonitrile compound can be produced in good yield by the present invention, the present invention is industrially applicable as a process for producing a mandelonitrile compound.

The invention claimed is:
1. A process for producing a mandelonitrile compound represented by formula (2):

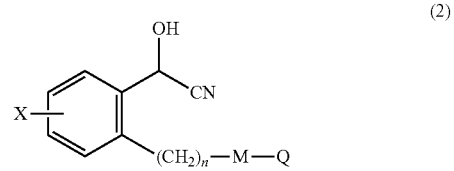

wherein Q represents an optionally substituted phenyl group X represents a hydrogen atom, M represents an oxy group (—O—), and n represents 1,
comprising a step of reacting a benzaldehyde compound represented by formula (1):

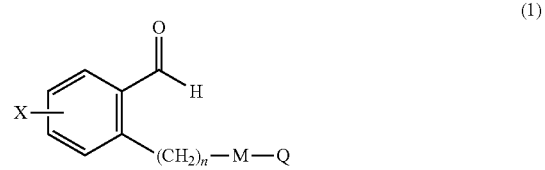

wherein Q, X, M and n are each as described above,
with at least one member selected from the group consisting of metal cyanides in the presence of a phase transfer catalyst in a solvent containing an alcohol.
2. The process according to claim 1, wherein the solvent is a mixed solvent composed of water, an alcohol and at least one member selected from the group consisting of aromatic hydrocarbons, aliphatic hydrocarbons and halogenated hydrocarbons.
3. The process according to claim 2, wherein the solvent is one adjusted to pH 6 to 8.
4. The process according to claim 3, wherein the solvent is one adjusted to pH 6 to 8 by mixing with acetic acid or hydrochloric acid.
5. The process according to claim 1, wherein the phase transfer catalyst is a quaternary ammonium salt, a quaternary phosphonium salt or a crown ether.

6. The process according to claim 1, wherein the phase transfer catalyst is at least one member selected from the group consisting of tetra-n-butylammonium bromide, benzyltriethylammonium chloride and methyltributylammonium chloride.

7. The process according to claim 1, wherein the use amount of the at least one member selected from the group consisting of metal cyanides is in the range of 1.2 mole to 3.0 mole with respect to 1 mole of the benzaldehyde compound represented by formula (1).

8. A process for producing a mandelonitrile compound represented by formula (2):

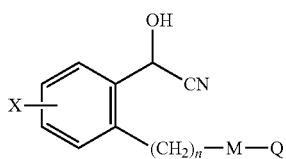

wherein Q represents an optionally substituted phenyl group X represents a hydrogen atom, M represents an oxy group (—O—), and n represents 1, comprising a mixing step of mixing a benzaldehyde compound represented by formula (1):

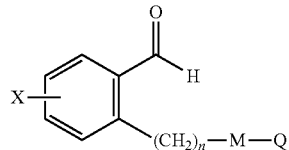

wherein Q, X, M and n are each as described above, at least one member selected from the group consisting of metal cyanides, a phase transfer catalyst, at least one member selected from the group consisting of aromatic hydrocarbons, aliphatic hydrocarbons and halogenated hydrocarbons, water, and an alcohol, and a step of adding an acid to the mixed liquid obtained in said mixing step, thereby maintaining the pH of the aqueous layer of the mixed liquid at 6 to 8.

9. The process according to claim 8, wherein the acid is acetic acid or hydrochloric acid.

10. The process according to claim 8, wherein the phase transfer catalyst is a quaternary ammonium salt.

11. The process according to claim 8, wherein the phase transfer catalyst is at least one member selected from the group consisting of tetra-n-butylammonium bromide, benzyltriethylammonium chloride and methyltributylammonium chloride.

* * * * *